(12) United States Patent
Lefevre

(10) Patent No.: US 8,008,029 B2
(45) Date of Patent: Aug. 30, 2011

(54) METHOD AND DEVICE FOR CHARACTERIZING CELLULAR COMPONENTS OF A BIOLOGICAL FLUID

(75) Inventor: Didier Lefevre, St. Clement de Riviere (FR)

(73) Assignee: Horiba ABX SAS, Montpellier (FR)

( * ) Notice: Subject to any disclaimer, the term of this patent is extended or adjusted under 35 U.S.C. 154(b) by 494 days.

(21) Appl. No.: 11/572,817

(22) PCT Filed: Jul. 6, 2005

(86) PCT No.: PCT/FR2005/001740
§ 371 (c)(1),
(2), (4) Date: Jan. 29, 2007

(87) PCT Pub. No.: WO2006/024716
PCT Pub. Date: Mar. 9, 2006

(65) Prior Publication Data
US 2008/0124745 A1 May 29, 2008

(30) Foreign Application Priority Data

Jul. 30, 2004 (FR) .................................... 04 08431

(51) Int. Cl.
*G01N 33/567* (2006.01)
*G01N 27/00* (2006.01)
*G01N 21/00* (2006.01)

(52) U.S. Cl. ..................... 435/7.21; 435/7.23; 435/7.24; 435/7.25; 435/287.1; 435/287.2; 436/8; 436/10; 436/63; 436/164; 436/165; 436/172; 422/73; 422/82.01; 422/82.02; 422/82.05; 422/82.07; 422/82.09; 422/98

(58) Field of Classification Search .................. 435/2, 6, 435/7.21, 7.24, 7.25, 40.5, 285.2, 173.5, 435/173.7, 7.23, 287.1, 287.2; 436/522, 436/46, 8, 10, 17, 18, 63, 164, 165, 169, 436/172, 175, 176; 422/51, 55, 73, 82.02, 422/82.07, 98, 82.01, 82.05, 82.09
See application file for complete search history.

(56) References Cited

U.S. PATENT DOCUMENTS

| | | | |
|---|---|---|---|
| 5,496,734 A * | 3/1996 | Sakata | 436/63 |
| 5,882,933 A | 3/1999 | Li et al. | |
| 6,228,652 B1 | 5/2001 | Rodriguez et al. | |
| 6,287,791 B1 * | 9/2001 | Terstappen et al. | 435/7.24 |
| 7,674,598 B2 * | 3/2010 | Paul et al. | 435/7.24 |

FOREIGN PATENT DOCUMENTS

FR 2 821 428 8/2002

OTHER PUBLICATIONS

Howard M. Shapiro, et al., "Combined Blood Cell Counting and Classification With Fluorochrome Stains and Flow Instrumentation", The Journal of Histochemistry and Cytochemistry, vol. 24, No. 1, XP 002058391, pp. 396-411, 1976.

* cited by examiner

*Primary Examiner* — Gail R Gabel
(74) *Attorney, Agent, or Firm* — Oblon, Spivak, McClelland, Maier & Neustadt, L.L.P.

(57) ABSTRACT

The invention concerns a method for differentiating and counting cellular components present in a biological fluid sample comprising a primary cytological analysis step typically implemented by a flow cytometry equipment (1) to obtain a set of primary results enabling the set of cellular components of the sample to be differentiated and counted in different populations; and a complementary step of cytological analysis of a particular type of cellular components, based on an identified cellular peculiarity, to obtain complementary results enabling at least one cell population or subpopulation of the sample to be differentiated and counted for identification of said cellular peculiarity. The invention is applicable in particular to hematological analyses.

19 Claims, 5 Drawing Sheets

METHOD AND DEVICE FOR CHARACTERIZING CELLULAR COMPONENTS OF A BIOLOGICAL FLUID

CROSS-REFERENCE TO RELATED APPLICATIONS

The present application is a 371 of PCT/FR05/01740 filed Jul. 6, 2005 and claims the benefit of French application 0408431 filed Jul. 30, 2004.

BACKGROUND OF THE INVENTION

1. Field of the Invention

The invention relates to a method for characterizing the cellular components of a biological fluid and for quantifying the populations and subpopulations of cells in the biological fluid, and a device which can be used to carry out the method.

Within the scope of the invention the phrase "biological fluid" refers to any natural fluid or biological preparation containing cellular components or capable of containing such components, such as blood, bone marrow, cerebrospinal fluid, pleural fluid, and the phrase "cellular component" also denotes a cell in its most conventional sense, such as red and white blood corpuscles, as well as any other cell type present in a biological fluid, such as platelets. Equally, the word "population" refers to a set of cells of the same category, for example, basophiles, lymphocytes, etc., and the term "subpopulation" denotes a subassembly of specific cells of the same category, such as B, T4, T8 lymphocytes, etc., of the lymphocyte population, but also immature or degenerate forms.

2. Description of Related Art

Determining and counting the entire cell population in various biological fluids such as blood are of major importance in terms of clinical diagnosis. The traditional methods of carrying out cytological analyses of a biological fluid make use of various conventional apparatus such as hematology machines based on flow cytometry, which are intended for differentiation and accurate automatic counting of all the cells present in a sample of biological fluid, which can then be classified into populations. These apparatus normally include measuring equipment, typically electrical, and/or optical, compatible with the possible presence of various reagents and dyes, leading to analysis results as defined above. Thus, for a blood sample, these automatic machines can draw up a hemogram which provides the classic parameters of a blood count, of the leukocyte formula and of platelet count. Using additional apparatus which are separate from one another it is possible to obtain additional results on the identification of reticulocytes, erythroblasts, immature cells, etc. in order to finalize the data of the hemogram. By way of example, reference may be made to patent application FR0102489 filed by the present applicant, which relates to a method and a reagent for the identification and counting of biological cells by multi-parametric methods of measurement making use of flow cytometry.

Thus it is possible to deduce information for each of the categories of biological cells, resulting in their classification.

In the great majority of cases the accurate automatic counting of all the cellular components and the differentiation of each of the populations of cellular components are sufficient to give the practitioner information as to the presence of an imbalance or a cytological disorder. However, when analyzing a biological fluid using a conventional automatic cytological analyzer, certain abnormal cell count results, compared with those which are normally expected, may justify further investigation in order to refine one or more of these results. Furthermore, such analysis does not accurately quantify the different populations of cells within a single population or family, which is a major drawback, particularly for detecting certain pathological conditions in patients or for monitoring their development.

Complementary analysis thus proves essential in order to achieve more accurate results on the count of a selected subpopulation of cells, e.g. leukocytes, in a blood sample. The appearance of certain pathological conditions (immune reactions or leukemia) may be correlated with an abnormal level of a leukocyte-type cell population.

Complementary analysis of this kind, independent of that carried out using a conventional machine, may consist in taking a manual smear followed by observation under the microscope. Identification and counting of cellular components are, in this case, currently used in addition to or as a replacement for those obtained using the automated equipment.

They may also consist of specific cell labeling using selected antibodies, possibly including fluorochromes, for discriminating a selected labeled cell population, or using any other labeling method known from the prior art. For example, mention may be made of patent application EP0552707, which discloses labeling using anti-CD45 and anti-CD71 monoclonal antibodies, for example, in order to differentiate all the leukocyte cells in flow cytometry. Patent Application WO00/16103 describes the quantification of eosinophilic and basophilic cells by discrimination thereof carried out using antibodies or an antibody kit and detecting them by fluorometry. Equally, the labeling of a lymphocyte population with anti-CD19, anti-CD4 and anti-CD8 antibodies makes it possible to separate the subpopulations of B lymphocytes, T helper lymphocytes and T suppressor lymphocytes, respectively.

Although these analyses can be used to monitor and/or correct the results obtained with a conventional automatic apparatus, they often introduce a degree of inaccuracy and allow only a statistical correlation with the results obtained using the automatic apparatus. The use of higher-performance methods such as flow cytometry produces substantially the same results, but a direct correlation with the results obtained using the automatic apparatus is not possible because two separate analyses are carried out, thus reducing the accuracy of the results as a whole.

In fact, when an analysis of the cellular components of an aliquot of biological fluid reveals an anomaly in the precise count of cellular components, the user goes on to perform a second independent analysis on a different aliquot of the same biological fluid, using two independent analysis systems, thus carrying out measurements on separate bases, i.e. each of the measurements supplies different results, and therefore mathematical correlation of the results obtained by each of the measurements is needed in order to obtain, eventually, results which contain errors. This leads to an interpretation of the results which takes on a subjective nature as it does not allow reliable identification of the real cause of the abnormal results, which may be due either to the sample itself or to the equipment and may also prove unacceptable for the precise diagnosis of a pathological condition, in some cases.

SUMMARY OF THE INVENTION

The present invention sets out to remedy the disadvantages of the prior art.

For this purpose it proposes a method for differentiating and counting the cellular components present in a sample of a biological liquid, comprising:

- a primary step of cytological analysis conventionally carried out by flow cytometry to obtain a set of primary results which allow differentiation and counting of all the cellular components of the sample in different populations; and
- an additional step of cytological analysis of a particular type of cellular components, based on an identified cellular peculiarity, in order to obtain complementary results enabling at least one cell population or subpopulation of the sample to be differentiated and counted for identification of said cellular peculiarity.

DETAILED DESCRIPTION OF THE INVENTION

Figure 1:
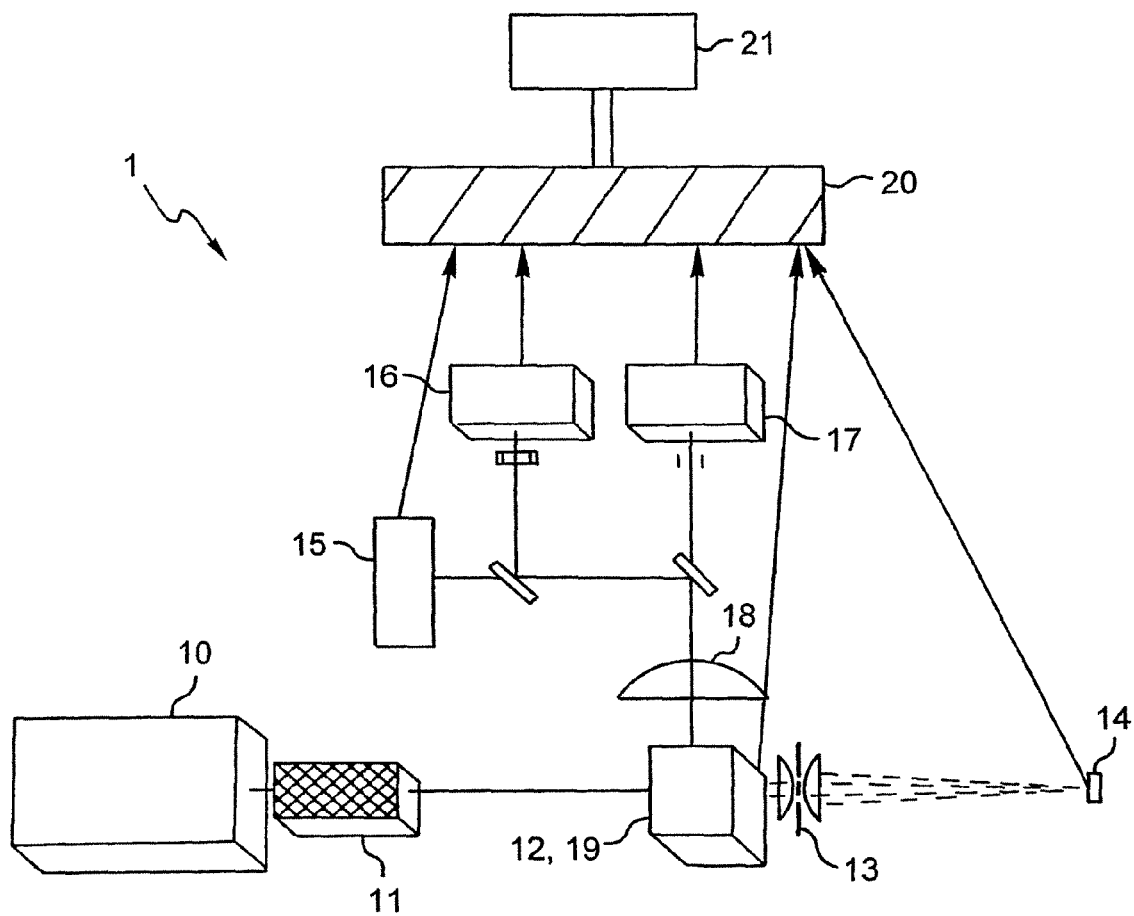
FIG. 1 shows a diagram of the specific elements that make up the analytical equipment according to a preferred embodiment.

Thus, the process according to the invention comprises a first step of conventional cytological analysis of a biological fluid or aliquot of biological fluid, conventionally carried out by flow cytometry, comprising electrical and/or optical measuring means and reagents representing a cell lysing agent, a dye for intracellular material, an aqueous diluent and mixtures thereof known to the skilled man. The signals coming from the above-mentioned measuring means are conventionally processed and converted into a "standardized series of results", i.e. a set of results which integrates the conventional parameters of the analysis. This therefore makes it possible to identify the cellular components and count them accurately, and these are then classified into different populations, as described for example in French Patent Application FR9701090.

The second step, or complementary step, makes it possible to obtain complementary results which can be used to identify the cellular peculiarity.

The results of an abnormal count on a particular category of cellular component or on a number of populations makes it possible to identify one or more anomalies. In the process according to the invention these anomalies may be linked, for example, to an abnormally high number of blasts or to lymphocytes of an abnormal structure.

In a preferred embodiment, first of all the single primary step is carried out and, if the primary results lead to the identification of at least one anomaly linked with an identified cellular peculiarity, the operator then proceeds to carry out the primary step, which is repeated in order to obtain a fresh set of primary results, and simultaneously the complementary step in order to obtain the complementary results linked with this cellular peculiarity.

Advantageously, the method further comprises a step of specific cell labeling, based on the identified cellular peculiarity, followed by a step of cytological analysis which will lead to all the primary results for identifying all the populations contained in the sample as well as the complementary results for identifying the population(s) or subpopulation(s) relating to the identified cellular peculiarity.

These peculiarities thus give rise to a specific labeling step of a particular type of cellular components, such as a subpopulation of lymphocytes in the blood, the number of which, in the blood aliquot, is abnormal compared with what would normally be expected, thus justifying a more intensive investigation for differentiating and counting this particular population in order to attempt to determine the different subpopulations thereof.

Once the labeling of the cellular components has thus been carried out it is then necessary to reveal the cellular components which have been specifically labeled or, as appropriate, those which have not been labeled. This is done by carrying out a complementary step of cytological measurement leading to additional results for quantifying and differentiating the cellular populations or cellular components of subpopulations which have been at the source of the anomaly or anomalies linked with their number or their presence. As already mentioned, the operator proceeds to carry out a repeat analysis of the primary analyses which are associated and simultaneous with the complementary step of the labeled cellular components. The results of these complementary measurements associated with those repeated from the primary analysis step obtained for the same aliquot of biological fluid thus supply, for the targeted subpopulation, results of differentiation and count which are established on a reference base identical to that which makes it possible to establish the standardized series of results. Any error or lack of precision inherent in successive analyses, in different analysis methods, in non-integrated equipment, is thus eliminated.

It will thus be possible to measure different physico-chemical characteristics on the same cellular component, notably by using a marker chosen for its specific affinity for at least one physico-chemical characteristic, such as the intracellular material (DNA, RNA), particular proteins or enzymes, membrane structure, etc. This makes it possible to differentiate each labeled cellular component from a non-labeled cellular component. The cellular components thus labeled or non-labeled are then detected by known methods (see description to follow). Equally, the cell labeling enables extremely accurate quantifying of the different subpopulations of the cellular components, such as the B, T4 and T8 lymphocytes, etc., of the lymphocyte population.

Consequently, carrying out the method according to the invention makes it possible to characterize peculiarities linked to the presence of certain cellular components characteristic of certain pathological conditions or to their abnormally low or high number in one and the same sample of biological fluid. It thus allows intracellular investigations to be carried out in a particular population or subpopulation. The method according to the invention offers these possibilities with results having a degree of precision and reliability which have never before been achieved, as the complementary analyses which correspond to these possibilities are carried out simultaneously and jointly with the analyses leading to the standardized series of results, thus guaranteeing the existence of a reference base which is common to all the complementary results and the standardized series of results, thus eliminating, in particular, all the disadvantages of separate analyses.

The method according to the invention also eliminates the overwhelming majority of errors of interpretation of the deviations observed from the standardized series of results, which may be subjected, as an anomaly, to a systematic standardized treatment.

The method according to the invention, in a single operation, produces full and extensive results, avoiding the need for successive multiple and separate analyses which might be prescribed by a practitioner in order to achieve an accurate pathological diagnosis. The advantage of this is that it reduces the costs associated with these analyses.

Similarly, in the case of pathologies which have been identified, for monitoring their development or the effectiveness of a treatment, the practitioner has a greater choice of analyses to prescribe which are carried out with the guaranteed reliability of a set of results relating to a single reference base.

Finally, the method according to the invention gives the practitioner greater reliability in detecting and characterizing the cellular peculiarities of the standardized series of results.

The primary step of cytological analysis advantageously comprises using the first measuring means for differentiating all the cellular components present in the sample by means of at least one electrical differentiating means including impedance or optical differentiating means including diffraction, diffusion, transmission and fluorescence.

Furthermore, this primary step may include the use of one or more reagents for differentiating all the cellular components present in the sample.

The complementary step of cytological analysis advantageously includes the use of secondary measuring means for differentiating and counting at least one cell population or subpopulation present in the sample of biological fluid.

The secondary measuring means preferably comprise the use of at least one optical differentiating means. Thus, these secondary measuring means preferably comprise one or more optical measuring methods capable of measuring, in a unitary or combined manner, optical parameters selected from among diffraction, transmission, fluorescence or absorbance, especially at certain wavelengths or certain ranges of wavelengths.

The secondary measuring means may consist of at least one measuring method operating with fluorescence and using one or more judiciously chosen wavelengths. In particular, the secondary measuring means may be operational at selected wavelengths ranging from ultraviolet to infrared.

Preferably, the specific cell labeling step comprises using at least one marker which can differentiate the cellular peculiarity, whereas the complementary step of cytological analysis comprises the use of secondary measuring means comprising at least one measuring method capable of identifying the marker or markers simultaneously with the set of measurements.

The processing of the measuring signals may be carried out using a computer comprising suitable means for processing data and compiling the results. These means may consist of two items of computing software, one of which is intended for processing the signals in order to provide a graphic display of the results and the other for processing the signals obtained from the analysis of the results. The computer may be combined with control means for controlling the specific cell labeling step.

In order to carry out the labeling step it is possible to use at least one cell marker representing a molecular probe selected from the group comprising at least one dye, at least one antibody conjugated with a dye or fluorochrome.

The dye chosen as a marker has to be different from the dye for the intracellular material in the predefined measurements, i.e. it must be detectable by optical measuring techniques at wavelengths which are different from those needed for detecting the dye in the predefined measurements.

Labeling with at least one antibody or a mixture of antibodies or antibody kit, which is conventionally carried out by antigen/antibody reactions, is carried out preferably using monoclonal antibodies onto which conventional dyes or fluorochromes have advantageously been grafted, such as fluorescein or phycoerythrin-cyanine 5 (PC5).

Moreover, for the analysis step, the electrical and optical measuring means represent, respectively, direct- or alternating-current cell impedance measuring means and measuring means selected from among light diffraction, light diffusion, light transmission or fluorescence.

Within the scope of the invention the biological fluid is preferably whole blood, diluted or undiluted, serum, diluted or undiluted bone marrow, cerebrospinal fluid, urine, synovial fluid, pleural fluid, etc.

When the sample of biological fluid is a blood sample, the primary step of cytological analysis advantageously comprises measurements needed to produce a hemogram including all or some of the parameters of cell counting, of leukocyte formula and of platelet counting.

In this case, the labeling step may be carried out by the use of specific marker antibodies for the cellular components of a blood sample selected from among the populations of red corpuscles, leukocytes and platelets. Thus, it is possible to carry out the process according to the invention by labeling targeted at the red corpuscles, in conjunction with labeling targeted at white corpuscles or platelets, without the risk of mutual interaction and interference in the analyses.

The labeling step is advantageously carried out by the use of specific antibodies for the cell labeling of at least one specific subpopulation present in a cell population of the blood sample.

Preferably, the labeling step is carried out by the use of specific antibodies for labeling at least one subpopulation selected from among the lymphocytes, neutrophils, basophiles, eosinophils, monocytes, red corpuscles, platelets, and all their precursors.

The cell labeling step may be carried out with at least one antibody or a mixture of antibodies conjugated with the fluorochrome, while the complementary step of cytological analysis uses cellular fluorescence-based measuring means of the orthogonal fluorescence type (FL2).

The cell labeling step is advantageously carried out with at least one antibody selected from among CD3, CD4, CD8, CD9, CD10, CD11b, CD13, CD14, CD15, CD16, CD18, CD19, CD20, CD21, CD22, CD33, CD34, CD45, CD63, CD64, CD71, CD203, CRTH2, FMC7 and HLA-DR.

The cell labeling step may also use at least one cell marker representing a molecular probe selected from among the group comprising at least one dye, at least one antibody conjugated with a dye or fluorochrome.

According to a further feature of the invention, the primary step of cytological analysis and the complementary step of cytological analysis simultaneously measure different physical characteristics of the same cellular components in the same flow.

The process according to the invention may include steps of mixing the reagent and the cell marker with the biological fluid and transferring the mixture thus obtained into an analysis cell, thus making it possible to carry out global and simultaneous analysis on the same biological fluid or aliquot of biological fluid, as explained hereinbefore.

The process according to the invention makes it possible to draw up, for a blood sample, for example, a complete hemogram, i.e. a detailed identification going beyond the standardized series of results and comprising the differentiation and counting of the cell populations in the blood, namely the lymphocytes, monocytes, erythrocytes, granulocytes, neutrophils, eosinophils and basophiles, the erythroblasts, the immature granular cells, the platelets, and other blasts, in conjunction with the possibility of detecting and counting, where present, a subpopulation of abnormal blasts in a lymphocyte population, which does not have a lymphocyte distribution conforming to what is expected. These lymphoblasts are isolated from the other lymphocyte populations according to their non-positivity to the anti-CD45 antibody, for example.

In another aspect the invention relates to an apparatus for carrying out the method described above, comprising equipment operating by flow cytometry having first measuring means comprising at least one measuring channel capable of measuring parameters selected from among optical parameters in the group made up of diffraction, diffusion, transmission and fluorescence and from an electrical parameter including impedance; secondary analyzing means comprising at least one measuring channel capable of measuring optical parameters selected from among diffraction, transmission, fluorescence and absorbance; and a computer for processing the results obtained from the first measuring means and secondary measuring means.

In a preferred embodiment the first measuring means comprise an axial diffraction sensor (FSC), an orthogonal diffusion sensor (SSC), an orthogonal fluorescence sensor (FL1) and a resistivity measuring electrode, whereas the secondary measuring means comprise an orthogonal fluorescence measuring sensor (FL2).

The equipment according to the invention thus comprises predefined conventional first analyzing means integrated in a flow cytometer. Advantageously, these means represent at least one measuring parameter or channel selected from among the group comprising the axial diffraction (FSC), orthogonal diffusion (SSC), orthogonal fluorescence (FL1) and resistivity (RES) of a sample or aliquot of biological fluid as described by the Applicant in patent application EP0425381. These first analyzing means therefore lead to the differentiation of the cellular components and to accurate counting thereof, enabling them to be classified into populations.

Advantageously, the primary means are arranged so as to incorporate at least one reagent for differentiating and counting all the cellular components of the biological fluid selected from the group comprising a cellular lysing agent, a dye for the intracellular material, an aqueous diluent and a mixture thereof, as described by the applicant in patent application FR0102489.

The lysing of certain cellular components of the biological fluid, particularly erythrocyte cells, is carried out for example using an ionic and/or non-ionic detergent which may represent the primary amides, cholamides, etc. The choice of lysing agent depends on the nature of the biological fluid and will therefore easily be determined by the skilled man.

The dye for the cellular components is intended to combine with the intracellular RNA or DNA. It may conventionally consist of thiazole orange, thiazole blue, etc. The reagent may optionally comprise a fixing agent for the cellular components, which is known in the art.

According to one embodiment of the apparatus according to the invention it further comprises:
 means for identifying at least one cellular peculiarity corresponding to the presence or the number of certain cell population(s) or certain cellular components,
 means for specific cell labeling as a function of the peculiarity identified.

The labeling means preferably comprise at least one cell marker representing a molecular probe selected from the group comprising at least one dye, at least one antibody which is associated with a dye or fluorochrome and, more preferably, they represent at least one antibody or antibody mixture with a fluorochrome grafted onto it.

According to one embodiment of the equipment according to the invention, the measuring means adapted to the labeling means constituting one or more measuring channels are respectively d.c. or a.c. cell impedance measuring means and at least one measuring means selected from the group comprising diffraction, light transmission and fluorescence or the absorbance of cells labeled at wavelengths ranging from ultraviolet to infrared.

Preferably, the measuring means based on cell fluorescence represent the orthogonal fluorescence of the fluorochrome (FL2) grafted onto a specific antibody.

According to a preferred embodiment of the apparatus according to the invention, it comprises a computer designed to carry out a correlation of the results from the first measuring means and the secondary measuring means and provide a graphic display of the results from the first measuring means and the secondary measuring means.

Advantageously, the computer is designed to carry out an interpretation and a classification of the cellular components according to their families or their physical characteristics.

The computer is designed to process the measuring signals and further comprises suitable means for processing the data and presenting the results, as described above. It preferably comprises memories for storing the results obtained by the various analyses.

It is possible that such apparatus may have an automatic decision-making capacity as to the appropriateness of carrying out analyses, in addition to the routine ones, needed to identify and count the elements which are being sought or which are suspected of being responsible for the anomalies detected.

The features and advantages of the invention will become more apparent from the detailed description that follows and from the non-restrictive embodiment by way of example, referring to the drawings attached hereinafter, wherein:

FIG. 1 shows a diagram of the specific elements that make up the analytical equipment according to a preferred embodiment;

FIGS. 2 to 19 show the diagrams of cell distribution or two-dimensional matrices obtained by means of multi-parametric measurements FSC, RES, SSC, FL1 and FL2.

In FIG. 1, the specific elements that make up the equipment 1 for analyzing an aliquot of biological fluid according to the invention are shown in the form of a functional diagram. This diagram partly makes use of the parameters described in patent application FR0102489. The equipment 1, an automatic apparatus based on flow cytometry, has the following parameters and components:

- a monochromatic laser 10,
- a device 11 for shaping the light beam,
- a circulation container 12 for measuring cellular volumes by resistivity and by optical measurement,
- an optical system 13 for collecting the radiation of axial diffraction (FSC),
- a sensor 14 of axial diffraction (FSC) providing an interpretation of size,
- a sensor 15 of orthogonal diffusion (SSC) expressing the structure of the cells observed,
- a sensor 16 of orthogonal fluorescence (FL1) measuring the expression of intracellular RNA and DNA,
- a sensor 17 of orthogonal fluorescence (FL2) measuring the reactivity of an antibody grafted with a fluorochrome,
- an optical system 18 for collecting orthogonal radiation,
- an electrode 19 for measuring resistivity (RES) incorporated in the container 12,
- a computer 20,
- a system 21 for displaying the results.

An aliquot of biological fluid is analyzed using the equipment 1 comprising the channels for optical measurement by axial diffraction, orthogonal diffusion and cellular orthogonal fluorescence, the principles of which are briefly set out below.

In the first case, a cell of the biological sample, placed in the measuring container 12, and through which light radiation emitted by the source 10 and shaped by the device 11 is passed, causes diffraction of the incident radiation the intensity of which is a function of the cell size. An optical system 13 for collecting the diffraction radiation is placed in alignment with the radiation. The diffracted radiation is collected on the sensor 14 the response of which is dependent on the cell diffraction.

The principle of orthogonal diffusion is based on measuring the diffusion of the light radiation passing through the cellular components. The radiation is collected at the sensor 15 orthogonally to the radiation diffused at the exit from the container 12 and the response is proportional to the diffusion.

The measurements of orthogonal fluorescence FL1 and FL2 are based respectively on the principle of excitation of a stained cell at a specific wavelength emitting fluorescent radiation with a different wavelength from the excitation wavelength and the excitation of the fluorochrome grafted onto a specific antibody which in turn emits specific fluorescence radiation.

An optical system 18 for collecting the orthogonal radiation FL1 and FL2 is placed orthogonally to the radiation emitted by the radiation source 10.

The equipment 1 also comprises a channel for electrical measurement by resistivity (RES). This measurement is based on the principle of placing an element in the container 12, in an electrical field where the current is constant and the resistance presented by this element in the field causes an increase in the voltage needed to keep the current constant, according to Ohm's law.

The electrodes 19 integrated in the container 12 measure the resistivity of the element, thus enabling its volume to be calculated.

EXAMPLE 1

One aliquot of normal blood is analyzed in a conventional automatic analyzer based on flow cytometry, as described in patent application FR 0102489, in order to characterize and quantify the leukocyte elements.

The results of this analysis are observed in the form of a two-dimensional matrix representing different combinations of measurement results obtained for each measuring channel. For the sake of clarity, the dots in each matrix representing each cellular element have been omitted. Only the contours delimiting each of the populations obtained have been drawn.

Figure 2:
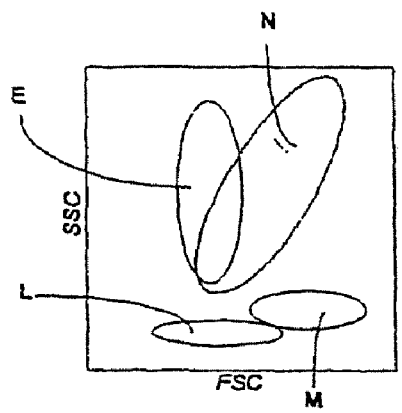
FIG. 2 shows a matrix obtained by means of axial diffraction and orthogonal diffusion.

FIG. 2 shows a matrix obtained by means of the two channels FSC and SSC. Four populations are observed: L representing the lymphocytes, M the monocytes, E the eosinophils and N the neutrophils. In this FIG. 1, the populations N and E are not clearly separated.

Figure 3:
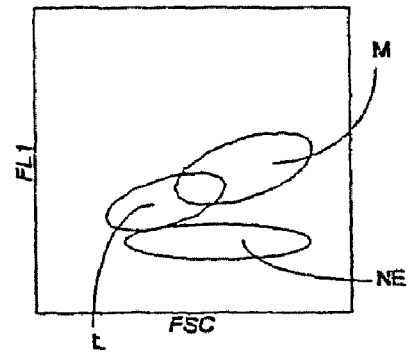
FIG. 3 shows a matrix obtained by means of an axial diffraction and orthogonal fluorescence.

FIG. 3 shows the matrix obtained by means of the two channels FSC and FL1. The populations N and E have merged and there is an overlap between the populations L and M.

Figure 4:
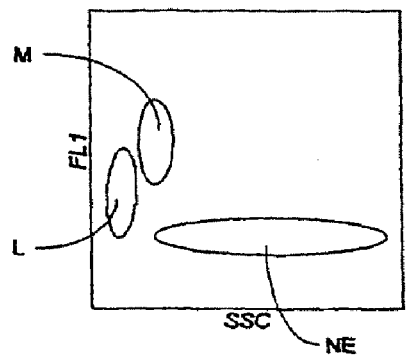
FIG. 4 shows a matrix obtained by measuring of orthogonal diffusion and orthogonal fluorescence.

FIG. 4 shows a matrix formed by the measuring channels SSC and FL1. The populations N and E have merged and the populations L and M are totally separate from one another.

Figure 5:
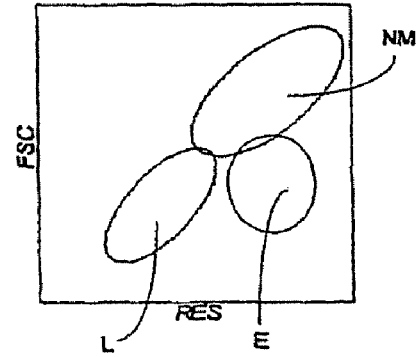
FIG. 5 shows a matrix obtained by measuring resistivity and axial diffraction.

FIG. 5 also shows a matrix formed by means of the two channels RES and FSC. In this arrangement, the populations L and E are separate but the populations N and M are not.

EXAMPLE 2

One aliquot of blood is analyzed in a conventional automatic analyzer based on flow cytometry, using the measuring channels described in patent application FR 0102489, in order to characterize and quantify the leukocyte components.

Figure 6:
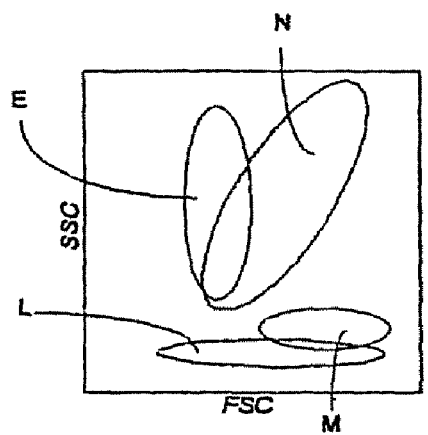
FIG. 6 shows a matrix obtained by using axial diffraction and orthogonal diffusion.
Figure 7:
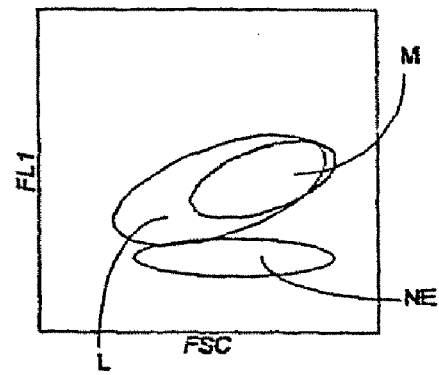
FIG. 7 shows a matrix obtained by means of an axial diffraction and orthogonal fluorescence.
Figure 8:
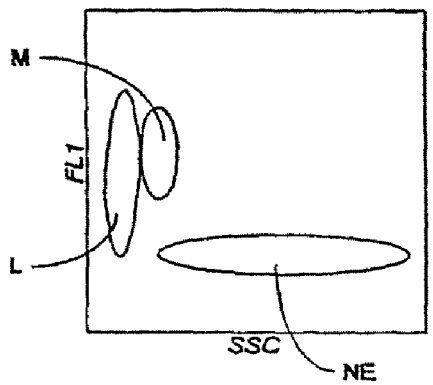
FIG. 8 shows a matrix obtained by measuring of orthogonal diffusion and orthogonal fluorescence.
Figure 9:
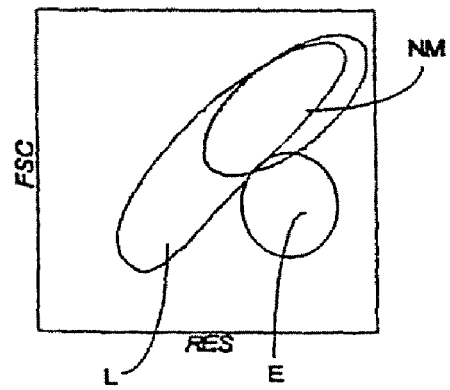
FIG. 9 shows a matrix obtained by measuring resistivity and axial diffraction.

FIG. 6 shows a matrix obtained using the two channels FSC and SSC. Even though the populations L and N have a profile similar to that in FIG. 2, by contrast the population L is abnormally extensive compared with the normal one shown in FIG. 2. This can also be seen in FIGS. 7 to 9 corresponding, respectively, to the matrix representations in FIGS. 3 to 5. At the end of these analyses, it seems probable that the lymphocyte population, the distribution of which in the diagram is more extensive than that of a normal lymphocyte population, has abnormal cellular elements such as blast cells.

EXAMPLE 3

One aliquot of blood from Example 2 is analyzed by the process according to the invention using the equipment 1.

This analysis is carried out as follows:

One aliquot of 50 μl of a human blood sample is taken, which is mixed with 50 μl of a solution of anti-CD45 monoclonal antibodies containing PC5 as fluorochrome. The solution thus obtained is incubated for some minutes, of the order of 3 to 30 minutes, in the absence of any light radiation and at ambient temperature. The solution thus obtained is then mixed with reagents containing, as intracellular dye, thiazole orange, to lyse the red corpuscles and fix the cellular elements needed to carry out the primary analysis steps.

In this case, the excitation wavelength of the thiazole orange using the laser 10 is 488 nm and that of the emission is 530 nm. The anti-CD45 antibody is used in this example for specifically labeling mature and normal leukocytes, in decreasing order of expression, the lymphocytes, eosinophils, monocytes, basophiles and neutrophils.

The solution is then transferred into the circulation container 12 of the analytical equipment 1. The user starts up the analyses of the aliquot in the four channels supplying conventional results for the differentiation and counting of the different cell populations, and in the fifth channel FL2 (excitation wavelength of the PC5 is 488 nm and that of the emission is 660 nm), using the computer 20 performing it simultaneously. The software goes on to process the results from each measurement using the channels defined above.

Figure 10:
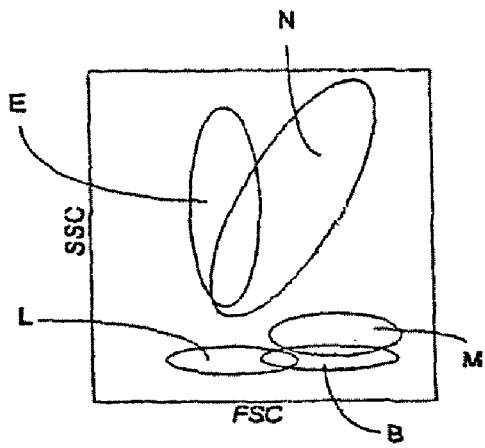
FIG. 10 shows a matrix obtained by measuring axial diffraction and orthogonal diffusion.

FIG. 10 shows a matrix obtained using the two channels FSC and SSC. Five populations are observed: L representing the lymphocytes, M the monocytes, E the eosinophils and B the blasts which are negative to the anti-CD45 antibodies.

In this FIG. 10, the populations N and E are not clearly separated and an overlap can be seen between the populations L, M and B.

Figure 11:
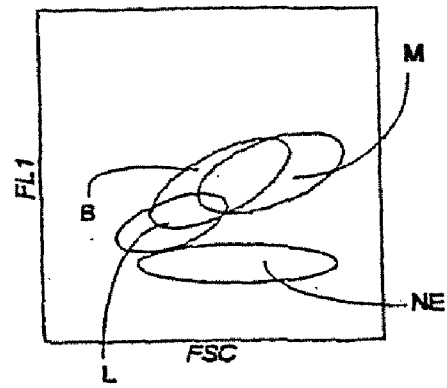
FIG. 11 shows a matrix obtained by means of axial diffraction and orthogonal fluorescence.

FIG. 11 shows the matrix obtained by means of the two channels FSC and FL1. The populations N and E have merged and an overlap can be seen between the populations L, M and B.

Figure 12:
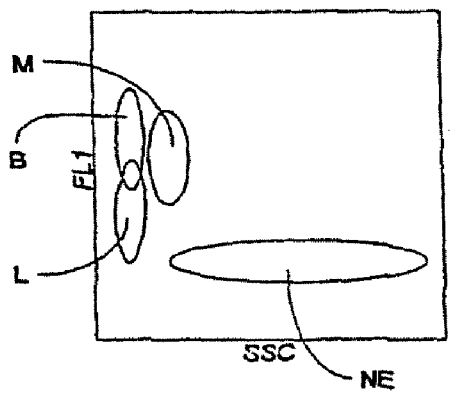
FIG. 12 shows a matrix obtained by orthogonal diffusion and orthogonal fluorescence.

FIG. 12 shows a matrix formed by the measuring channels SSC and FL1. The populations N and E have also merged and although the population M is separate from the others, it can be seen that the populations B and L are not entirely separate.

Figure 13:
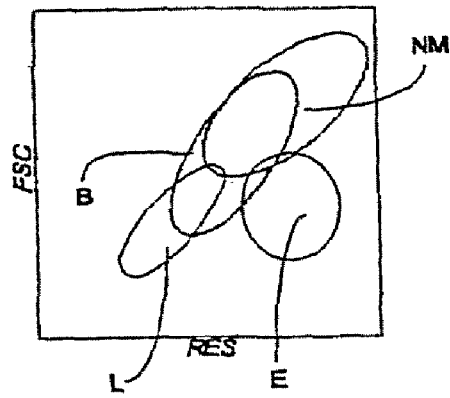
FIG. 13 shows a matrix obtained by measuring resistivity and axial diffraction

FIG. 13 also shows a matrix formed by means of the two channels RES and FSC. In this arrangement, none of the populations present is clearly separate.

Figure 14:
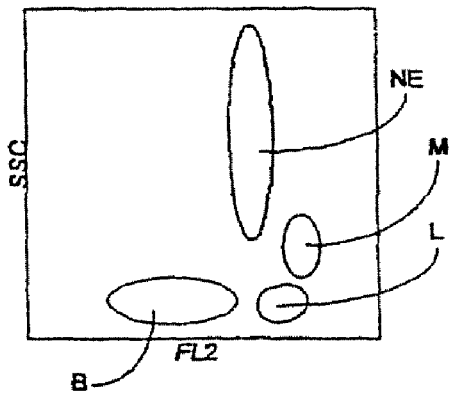
FIG. 14 shows a matrix obtained by orthogonal fluorescence and orthogonal diffusion.

FIG. 14 shows a matrix formed by means of the two channels FL2 and SSC. This matrix view makes it possible to separate the population of abnormal blasts B from the lymphocyte population.

By carrying out the process using the equipment 1 according to the invention it is possible to characterize and quantify the presence of blasts B (negative to anti-CD45) in the aliquot of blood analyzed. The complementary measurement shown in FIG. 14 allows clear differentiation of the blasts B, something which was not possible with all the predefined measurements of the hemogram.

EXAMPLE 4

This example is intended to provide a precise count of the non-blastic cellular components in a blood sample, the blast population of which is known, within the framework of the monitoring of treatment in a patient. Previous analyses have shown an abnormal distribution of the lymphocyte population, justifying further checks.

The analysis that follows is intended to identify lymphocyte elements to enable them to be counted accurately.

This identification will be done using anti-CD19 and anti-CD3 antibodies conjugated with the same fluorochrome PC5 and by detection of the labeled lymphocytes by means of the channel FL2.

One aliquot of 50 µl of blood with a known blastic population is analyzed on the equipment 1 described earlier and subjected to the analytical steps and reagents described in Example 3.

Figure 15:
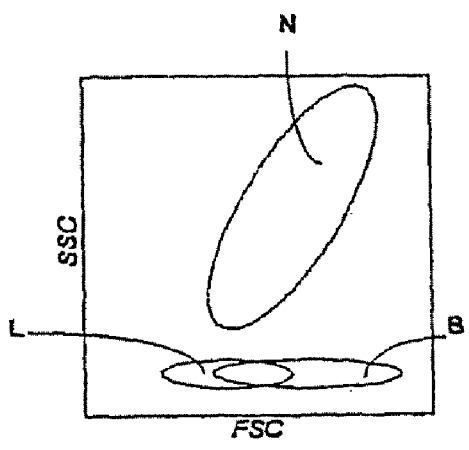
FIG. 15 shows a matrix obtained by axial diffraction and orthogonal diffusion.
Figure 16:
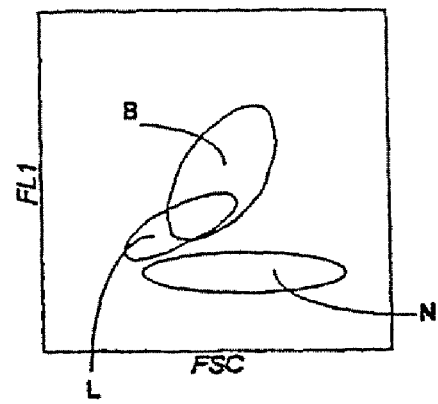
FIG. 16 shows a matrix formed by means of the two channels FSC and FL1.
Figure 17:
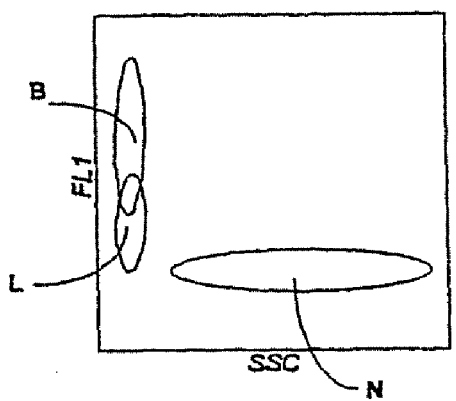
FIG. 17 shows a matrix formed by means of the two channels SSC and FL1.
Figure 18:
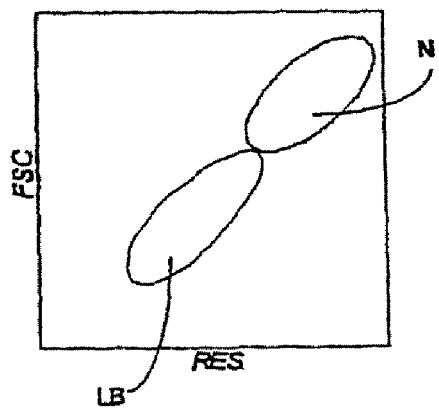
FIG. 18 shows a matrix formed by means of the two channels RES and FSC.

FIG. 15 shows a matrix obtained by means of the two channels FSC and SSC. Three populations are observed: L for the lymphocytes positive to labeling by the anti-CD3 and anti-CD19, N for the neutrophils and B for the lymphocyte elements negative to these two antibodies. The population N is not totally distinct from the other two, L and B, which are observed to have a degree of inter-population overlap. This can also be seen in FIGS. 16 to 18 corresponding, respectively, to the matrix representations according to the arrangements in FIGS. 3 to 5.

Figure 19:
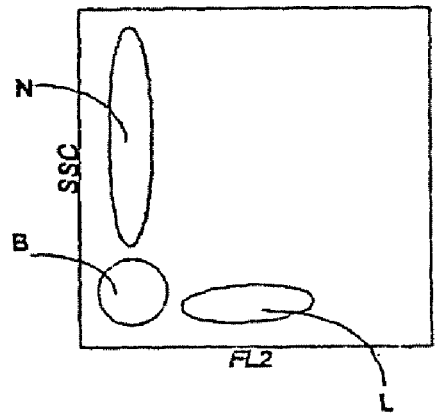
FIG. 19 shows a matrix formed by means of the two channels FL2 and SSC.

FIG. 19 shows a matrix formed by means of the two channels FL2 and SSC. This matrix view makes it possible to separate the three populations under consideration and especially to separate the lymphocytes which are positive from those which are negative to anti-CD3 and anti-CD19 over the whole of the leukocyte formula, thus enabling an accurate count to be taken. The complementary measurement shown in FIG. 19 allows clear differentiation of the lymphocytes positive to CD3 antibodies and to CD19 antibodies, something which was not possible with all the predefined measurements of the hemogram.

The invention claimed is:

1. A method of differentiating and counting cells present in a sample of a biological fluid, wherein the method comprises:
   (1) subjecting said sample to flow cytomeric analysis comprising measuring all of the cells present in the sample to be differentiated by electrical differentiation including impedance or an optical differentiation comprising diffraction, diffusion, transmission or fluorescence in a flow cytometer to obtain a set of primary results,
   (2) differentiating the cells of the sample into different populations and count the cells in each of the different populations, wherein the differentiating and counting are based on the primary results,
   (3) identifying the presence or absence of at least one anomaly in said set of primary results, wherein the anomaly is linked to an identified cellular peculiarity,
   (4) in response to identifying the presence of at least one anomaly identified in step (3), repeating the subjecting step in (1) and the differentiating step in (2) and further performing simultaneously steps (5) and (6) using the same aliquot of biological cell sample,
   (5) subjecting the sample to a further flow cytometric analysis in the flow cytometer, wherein the further flow cytometric analysis is based on the identified cellular peculiarity wherein the sample is tagged with a cell-specific dye or a cell-specific antibody conjugated to a dye or fluorochrome and the further flow cytometric analysis yields complementary results, and
   (6) differentiating the cells of the sample into different populations and/or subpopulations and count the cells in each of the different populations and/or subpopulations, wherein the differentiating and counting are based independently on the combination of the primary result, the repeated primary result, and the complementary result.

2. The method according to claim 1, wherein the flow cytometric analysis (1) comprises one or more reagents that differentiate all the cells present in the sample.

3. The method according to claim 1, wherein the flow cytometric analysis (5) comprises measuring at least one cell population or subpopulation present in the sample of biological fluid to be differentiated and counted.

4. The method according to claim 3, wherein the measuring comprises at least one optical differentiation.

5. The method according to claim 4, wherein the measuring comprises measuring at a predetermined wavelength, in a unitary or combined manner, optical parameters selected from the group consisting of diffraction, transmission, fluorescence and absorbance.

6. The method according to claim 5, wherein the measuring comprises at least one of fluorescence measurement at one or more predetermined wavelengths.

7. The method according to claim 6, wherein the fluorescence measurement operates at selected wavelengths ranging from ultraviolet to infrared.

8. The method according to claim 1, wherein the cell specific labeling comprises labeling with a cell-specific antibody conjugated to a dye or fluorochrome, and wherein the cytological analysis (5) comprises a secondary measurement capable of identifying the marker(s) simultaneously with the measurement (1).

9. The method according to claim 8, wherein the cell specific labeling comprises a single cell-specific antibody conjugated to a dye or fluorochrome.

10. The method according to claim 1, wherein the sample of biological fluid is selected from the group consisting of: diluted whole blood, undiluted whole blood, diluted non-whole blood cell sample, and undiluted non-whole blood cell sample.

11. The method according to claim 1, wherein the sample of biological fluid is a blood sample and wherein the flow cytometric analysis yields a haemogram comprising cell count, leukocyte formula, platelet count, or a combination thereof.

12. The method according to claim 1, wherein the sample of biological fluid is a blood sample and wherein the cell specific labeling comprises cell-specific antibodies conjugated to a dye or fluorochrome for the cells of the blood sample, wherein the cell-specific antibodies are specific for red corpuscles, leukocytes or platelets.

13. The method according to claim 12, wherein the cell specific labeling comprises cell-specific antibodies conjugated to a dye or fluorochrome for at least one specific subpopulation present in a cell population of the blood sample.

14. The method according to claim 12, wherein the cell specific labeling comprises cell-specific antibodies conjugated to a dye or fluorochrome for at least one subpopulation selected from the group consisting of lymphocytes, neutrophils, basophils, eosinophils, monocytes, red corpuscles, platelets, and their precursors.

15. The method according to claim 1, wherein the cell specific labeling comprises at least one cell-specific antibody conjugated to a dye or fluorochrome or a mixture of cell-specific antibodies conjugated with a fluorochrome, and wherein the flow cytometric analysis (5) comprises cellular fluorescence of the orthogonal fluorescence type.

16. The method according to claim 1, wherein the cell specific labeling comprises at least one cell-specific antibody specific for an antigen selected from the group consisting of CD3, CD4, CD8, CD9, CD10, CD11b, CD13, CD14, CD15, CD16, CD18, CD19, CD20, CD21, CD22, CD33, CD34, CD45, CD63, CD64, CD71, CD203, CRTH2, FMC7 and HLA-DR.

17. The method according to claim 1, wherein the cell specific labeling comprises at least one cell-specific dye, at least one cell-specific antibody conjugated with a dye or a fluorochrome.

18. The method according to claim 1, wherein the flow cytometric analysis (1) and the flow cytometric analysis (5) simultaneously measure different physical characteristics in the flow cytometer.

19. The method according to claim 1, wherein the sample of biological fluid is selected from the group consisting of serum, diluted bone marrow, undiluted bone marrow, cerebrospinal fluid, urine, synovial fluid, and pleural fluid.

* * * * *